United States Patent [19]
Suresh

[11] Patent Number: 6,156,003
[45] Date of Patent: *Dec. 5, 2000

[54] SURGICAL VISUALIZATION AND MOISTURIZING DEVICE

[75] Inventor: Mitta Suresh, Richardson, Tex.

[73] Assignee: Chase Medical, Inc., Richardson, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 09/076,393

[22] Filed: May 12, 1998

[51] Int. Cl.$^7$ .................................................. A61M 37/00
[52] U.S. Cl. .................................. 604/24; 604/23; 604/48
[58] Field of Search .................................. 604/22–26, 43, 604/523, 264, 171, 45, 48, 500, 902, 275

[56] References Cited

U.S. PATENT DOCUMENTS

| | | |
|---|---|---|
| Re. 31,873 | 4/1985 | Howes . |
| 1,114,268 | 10/1914 | Kells . |
| 2,029,141 | 1/1936 | Warner . |
| 3,771,527 | 11/1973 | Ruisi . |
| 4,108,178 | 8/1978 | Betush . |
| 4,149,535 | 4/1979 | Volder . |
| 4,357,940 | 11/1982 | Muller . |
| 4,468,216 | 8/1984 | Muto ........................................... 604/43 |
| 4,834,702 | 5/1989 | Rocco ......................................... 604/43 |
| 4,941,872 | 7/1990 | Felix et al. ................................. 604/27 |
| 5,106,368 | 4/1992 | Uldall et al. ............................... 604/43 |
| 5,163,433 | 11/1992 | Kagawa et al. . |
| 5,336,170 | 8/1994 | Salerno et al. ............................. 604/24 |
| 5,464,389 | 11/1995 | Stahl ........................................... 604/22 |
| 5,591,184 | 1/1997 | McDonnell et al. ...................... 606/167 |
| 5,626,560 | 5/1997 | Soring ........................................ 604/22 |
| 5,713,849 | 2/1998 | Bosma et al. .............................. 604/28 |
| 5,735,813 | 4/1998 | Lewis .......................................... 604/43 |
| 5,800,384 | 9/1998 | Russell et al. ............................. 604/43 |
| 5,882,347 | 3/1999 | Mouris-Laan et al. ................... 604/280 |
| 5,908,446 | 6/1999 | Imran ......................................... 607/122 |

FOREIGN PATENT DOCUMENTS 176 789A  8/1922  United Kingdom .

Primary Examiner—Wynn Wood Coggins
Assistant Examiner—LoAn H. Thanh
Attorney, Agent, or Firm—Jackson Walker, LLP

[57] ABSTRACT

A surgical visualization and moisturizing device providing improved visualization and moisturizing of a surgical site such as an anastomosis. The device of the present invention is provided with a plurality of small flexible lumens extending through and terminating distal of a gas flow port to thoroughly mix and moisture the gas flow with a saline solution. Each of the plurality of flexible lumens, preferably forming a ribbon, are separated from one another slightly at the distal tip to permit vibration due to the gas flow exiting about and past each of the saline lumens. This spacing further facilitates uniform moisturizing of the gas flow. The distal ends of the saline lumens extend beyond the tip of the device such that the pressure of the gas flow approaches atmospheric pressure, whereby gas flow will not go against the head pressure of the saline bag. This eliminates the need for a pressure cuff on the saline bag. The present invention further minimizes dripping at the distal tip, further improving visualization of an anastomosis site for the surgeon.

19 Claims, 1 Drawing Sheet

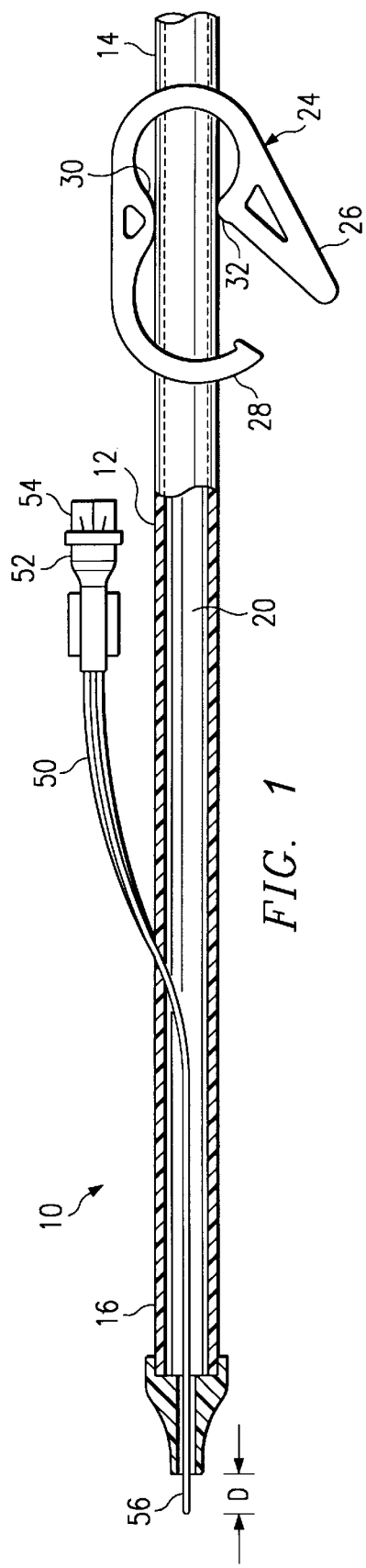
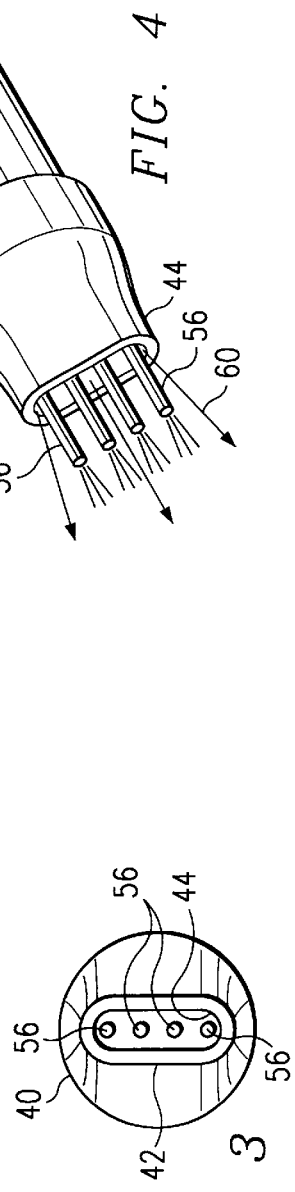
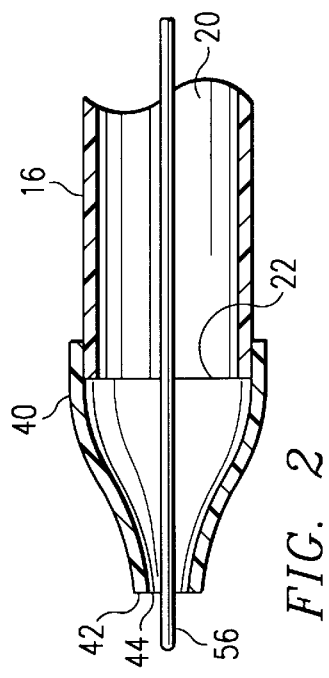

SURGICAL VISUALIZATION AND MOISTURIZING DEVICE

FIELD OF THE INVENTION

The present invention is generally related to surgical instruments and procedures, and more specifically to an apparatus including wands for enhancing visualization of an anastomosis site during surgery, including removing excess bodily fluids from the anastomosis site during anastomosis procedures.

BACKGROUND OF THE INVENTION

With the advent of minimally invasive procedures in all fields of surgery, the importance of new surgical tools to help surgeons has become all more critical. One such device is an anastomosis visualization device. Anastomosis is a surgical procedure including attaching one blood vessel to another. An anastomosis visualization device is updated to clear fluids and help the surgeon see or visualize a suturing site better. Blood in arteries can spew out from the anastomosis site during surgery, which in turn reduces visualization for the surgeon. Spewing of blood and other bodily fluids can occur, for instance, during a coronary bypass procedure whereby a blood vessel is attached to the coronaries, which may occur while the heart is beating or arrested. During anastomosis, an incision is made in the coronary artery, and then a blood vessel is attached by suturing the blood vessel around the incision.

There are some products available on the market to enhance visualization. These products are primarily designed to blow carbon dioxide gas on the anastomosis site, this gas clearing the blood from the site as soon as it oozes out of the artery. However, it has been found that simply blowing dry carbon dioxide actually dries up the surface of the heart and the site, which is undesired. To address this shortcoming, some devices available on the market are designed to moisten the gas. One such device is described in Salerno U.S. Pat. No. 5,336,170. This device has two inlets, one for receiving gas, and the other for receiving a liquid such as saline solution. This particular device has a tip, whereby saline solution is permitted to drip inside the tip. The saline solution mixes with the gas to provide a moistened gas. One of the drawbacks of the Salerno device is that when the flow of gas is increased, the gas pressure in the tip is higher than the pressure inside the source saline bag. In this situation, the gas actually forces itself into the saline bag. To avoid this drawback and to make sure the saline is actually flowing into the gas stream, the surgical staff typically has to use a pressure cuff on the saline bag to keep the pressure inside the bag to be higher than that of the gas forcing itself into the bag. Another problem with the Salerno device is that the saline drips from the tip. Dripping at the tip of this device occurs primarily because all of the saline dripping into the gas stream is not moisturizing. This dripping can be a nuisance to the surgeon during an anastomosis procedure.

There is desired an improved visualization and moisturizing device which provides an improved moistened gas flow without requiring a pressure cuff on the saline bag, and which does not create dripping at the tip.

SUMMARY OF THE INVENTION

The present invention derives technical advantages by providing at least one, and preferably a plurality, of relatively small flexible saline lumens extending within and slightly outward from the distal end of a gas lumen to facilitate moisturizing a gas flow exiting therefrom. Since the tips of the moisturizing lumens extend slightly beyond the outlet of the gas lumen, the gas flow is at atmospheric pressure and will not go against the head pressure of the saline bag. The present invention also derives technical advantages by preventing dripping at the tip. By providing a plurality of small diameter saline lumens, preferably together formed as ribbon, smaller drops of saline will be injected into the gas stream flowing therepast thereby moistening the gas stream without dripping.

The saline lumens or tubes extending from the gas lumen for injecting the saline solution into the gas flow typically have an inner diameter of between about 0.010 to 0.060 inches. It has been found that the inner diameter of these lumens should not be less than 0.010 inches to allow free flow of saline solution from a saline bag. These individual tubes are joined in a ribbon to form a bundle, but wherein these individual lumens are separated from one another at their distal tips. This separation of the saline lumens from one another at the outlet port of the gas lumen allows the saline lumens to move and vibrate while the gas is flowing therepast, which vibration further helps to moisture the gas flow better. The saline drops being injected into the gas flow will wash into the gas before they coalesce.

BRIEF DESCRIPTION OF THE DRAWINGS

FIG. 1 is a cross section of a surgical visualization and moisturizing device according to the preferred embodiment of the present invention illustrating a ribbon of small saline lumens extending through and terminating slightly outward from an outlet of a gas flow lumen to facilitate moisturizing the gas flow exiting therefrom;

FIG. 2 is an exploded view of the tip of the device in FIG. 1 illustrating a side view of the planar ribbon comprising multiple saline lumens extending slightly outward from the distal tip of the gas flow lumen outlet;

FIG. 3 is an end view of the device of FIG. 1 illustrating the plurality of small saline lumens being separated from one another such that they are permitted to vibrate and move and gas flow exits therepast from the gas lumen to further facilitate moisturizing the gas stream; and FIG. 4 is a perspective view of the present invention of FIG. 1 in use illustrating saline solution being injected from the saline lumens into the gas flow flowing therepast to form a planar moistened third flow.

DESCRIPTION OF THE PREFERRED EMBODIMENT

Referring now to FIG. 1, there is generally shown at a surgical visualization and moisturizing device according to the preferred embodiment of the present invention. Device is seen to include an elongated tubular body 12 having a proximal end 14 and a distal end 16. Tube body 12 may be comprised of stainless steel, polyvinylchloride or other suitable materials. Extending within tube body 12 is an elongated lumen extending from the proximal end 14 to the distal end 16 and terminating at a distal port 22, as shown in FIG. 2. A flexible plastic pinch clamp 24 of a type known in the art is disposed about the delivery tubing 12 for the selective partial or total occlusion of lumen by pinching of the delivery tubing 12 to stop the gas stream flowing therethrough from a gas source (not shown) without altering the gas flow source adjustment. Engagement of the leg 26 with the inner surface of the leg 28 locks clamp 24 in a closed position, wherein delivery tube 12 will be totally collapsed between pinched bars 30 and 32 of clamp 24.

Referring to FIG. 1 and FIG. 2, there is seen at the distal end 16 of tube body 12 a tapering tip 40 which is secured to and disposed about the distal end 16. Tip 40 tapers to a distal end 42 forming an elongated outlet port 44, as shown in FIG. 3. This elongated outlet port 40 creates a planar moisturized fluid flow exiting therefrom for good control in use.

Referring back to FIG. 1 and FIG. 2, there is seen a planar ribbon of saline lumens generally depicted at 50 extending from an adapter member 52 having a vented male luer lock cap 54 secured thereto, into the tubular member 12 at a mid section thereof. The ribbon of saline lumens 50 extends through and into the gas flow lumen 20, extending through the distal port 22 of member 12 as well as the opening 44 of the tip member 40 as shown in FIG. 1 and FIG. 2. Each of the individual lumens, being shown at 56, freely extend through the elongated opening 44 of tip 40 where each lumen 56 is separated from one another slightly, as shown in FIG. 3. Each lumen 56 is preferably comprised of a flexible material such as PVC. Each lumen 56 extends slightly outward from the distal opening 44 of tip 40, preferably about 1/32 inches, although this distance can vary. It is to be understood that only one lumen 56 is required, but several are preferred to achieve an effective moisturization of the gas flow.

This distance is represented as D, whereby this distance D can vary, but should be sufficient such that the distal ends of lumens 56 terminate at approximately the ambient pressure when a gas flow is exiting from port 44, thereby preventing the gas flow exiting port 44 from forcing its way back into lumens 56 and into a saline bag (not shown) attached to port 54. In a preferred embodiment, the spacing of each of the lumens 56, as shown in FIG. 3, is approximately 0.1 inches, but limitation to this dimension is not to be inferred. Rather, it is preferred that the spacing of each lumen 56 from one another be sufficient to allow movement and vibration of the free end of lumen 56 when a gas flow exits through port 44 to allow a saline fluid exiting lumens 56 to thoroughly mix and moisturize the gas flow encompassing the outlet ports 56. As shown in FIG. 3, the inner diameter of the lumen 56 is substantially smaller than the overall cross sectional area of tip outlet port 44, and to achieve good moisturizing of the gas flow without dripping. In addition, the total cross sectional area of each flexible lumens 56 is substantially less than the cross sectional area of port 44 to prevent restriction of gas flow from exiting port 44.

Referring to FIG. 4, there is shown a perspective view of the device 10 in use. A gas source, such as carbon dioxide, is connected to the inlet end of lumen 20 and caused to flow to and exit from the tip opening 44 about the distal ends of each of the lumens 56. A saline bag (not shown) is connected to luer lock cap 54 to provide a saline source to each of the lumens 56 of ribbon 50. Head pressure of this saline bag causes saline solution to flow through each of the lumens 56 and dispense out the distal ends of the lumens 56, thereby mixing with the gas flow flowing past and about each of the lumens 56. Since the inner diameters of each lumens 56 is relatively small, again, preferably in the range of between 0.010 inches and 0.060 inches to ensure free flow of saline solution therethrough, and preferably not less than 0.010 inches, the saline solution thoroughly mixes and moisturizes the gas flow shown at 60 ejecting from the port 44 of distal tip 40. Moreover, due to the gas flow 60 exiting the port 44, the separated distal tips 56 vibrate, further insuring that saline solution dispensing from each of the lumens 56 does not coalesce or cause dripping from the tip of device 10. Since the distal ends of lumens 56 each extend distally of the outlet port 44, the gas flow 60 is approaching atmospheric pressure, and will not go against the head pressure of the saline bag. This feature derives technical advantages in that the surgical staff will not need to apply a pressure cuff on the saline bag. By providing multiple separated small lumens 56, very small drops are injected into the gas stream providing a large surface area of the saline for a given volume of gas flow. The distal tip is tapered, as shown, to create a planar moisturized gas flow which is well suited for controllably clearing fluids from a surgical site, such as an anastomosis. It is to be recognized that the present invention is well suited for other surgical procedures as well, and application for an anastomosis is one preferred use and is discussed by way of illustration to teach the various advantages and features of the present invention.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications.

We claim:

1. A device for delivering a fluid stream having a gas component, comprising:

a tubular body having a first lumen having an inlet end for receiving the gas component and an outlet end; and a plurality of second lumens each having a distal end extending within a portion of said first lumen outlet end adapted to deliver liquid into said gas component flowing from said first lumen, wherein a portion of each said second lumen distal ends extend beyond said first lumen outlet end and are not encompassed by any structure.

2. The device as specified in claim 1 wherein said second lumen distal ends are freely positioned within said first lumen outlet end such that said second lumen distal ends are movable within said first lumen outlet end when the gas component flows therethrough to facilitate moisturizing the gas component.

3. The device as specified in claim 2 wherein said first lumen outlet end is tapered.

4. The device as specified in claim 3 wherein said first lumen outlet end tapers to shape a gas flow therethrough to a planar flow.

5. The device as specified in claim 3 wherein said second lumen distal ends are spaced from one another by at least 0.10 inches.

6. The device as specified in claim 1 wherein said second lumen distal ends are generally coplanar with each other at said first lumen outlet end.

7. The device as specified in claim 6 wherein said first lumen outlet end is elongated and extends parallel to said coplanar second lumen distal ends.

8. The device as specified in claim 7 wherein said second lumen distal ends extend within a central portion of said first lumen outlet end such that gas exiting said first lumen outlet end flows about said second lumen distal ends.

9. The device as specified in claim 1 wherein a collective cross sectional area of said second lumens is substantially less than a cross section of said first lumen.

10. The device as specified in claim 9 wherein said second lumens comprise a ribbon.

11. The device as specified in claim 1 wherein said second lumens each have a diameter substantially smaller than a diameter of said first lumen outlet end.

12. The device as specified in claim 1 wherein each said second lumen distal end is free and movable with respect to another said second lumen distal end when the gas component flows through said first lumen to facilitate moisturizing the gas component.

13. The device as specified in claim 1 wherein said second lumen distal end extends within a central portion of said first lumen outlet end such that gas exiting said first lumen outlet end flows about said second lumen distal end.

14. The device as specified in claim 1 wherein said second lumen extends beyond said outlet end of said first lumen about 1/32 inches.

15. The device as specified in claim 1 wherein said second lumen has an inner diameter in a range of between 0.010 and 0.060 inches.

16. The device as specified in claim 1 wherein said second lumens each have an inner diameter in a range of between 0.010 and 0.060 inches.

17. The device as specified in claim 1 wherein said second lumen distal end is flexible to permit vibration thereof when the gas component flows therepast from said first lumen.

18. The device as specified in claim 1 wherein each said second lumen distal end is flexible to permit vibration when the gas component flows therepast from said first lumen.

19. A method of using a device comprising:

a tubular body having a first lumen having an inlet end for receiving a gas component and an outlet end; and at least one second lumen having a distal end extending within a portion of said first lumen outlet end adapted to deliver liquid into said gas component flowing from said first lumen, wherein a portion of said second lumen distal end terminates beyond said first lumen outlet end and said portion of said second lumen distal end is not encompassed by any structure;

comprising the steps of:

injecting a fluid via said second lumen into a gas stream flowing past the distal end of said second lumen from said first lumen to thereby moisturize the gas stream.

* * * * *